United States Patent
Xu et al.

(10) Patent No.: US 11,920,175 B2
(45) Date of Patent: Mar. 5, 2024

(54) METHOD FOR EXTRACTING AND ISOLATING LUTEIN CRYSTAL FROM VEGETABLE OIL RESIN CONTAINING LUTEIN DIESTER

(71) Applicant: Zhejiang Medicine Co., Ltd. Xinchang Pharmaceutical Factory, Shaoxing (CN)

(72) Inventors: Xinde Xu, Shaoxing (CN); Tian Xie, Shaoxing (CN); Shengfan Wang, Shaoxing (CN); Qiuyan Wang, Shaoxing (CN); Jianyong Zheng, Shaoxing (CN); Zhaowu Zeng, Shaoxing (CN); Xiaopu Yin, Shaoxing (CN); Xuejun Lao, Shaoxing (CN); Kangzhong Shao, Shaoxing (CN)

(73) Assignee: ZHEJIANG MEDICINE CO., LTD. XINCHANG PHARMACEUTICAL FACTORY, Zhejiang (CN)

( * ) Notice: Subject to any disclaimer, the term of this patent is extended or adjusted under 35 U.S.C. 154(b) by 543 days.

(21) Appl. No.: 17/259,161

(22) PCT Filed: Jul. 9, 2019

(86) PCT No.: PCT/CN2019/095327
§ 371 (c)(1),
(2) Date: Jan. 9, 2021

(87) PCT Pub. No.: WO2020/011176
PCT Pub. Date: Jan. 16, 2020

(65) Prior Publication Data
US 2021/0147353 A1    May 20, 2021

(30) Foreign Application Priority Data

Jul. 10, 2018 (CN) .......................... 201810753839.0
Aug. 29, 2018 (CN) .......................... 201810992984.4

(51) Int. Cl.
*C07C 403/24* (2006.01)
*C12P 23/00* (2006.01)

(52) U.S. Cl.
CPC ............ *C12P 23/00* (2013.01); *C07C 403/24* (2013.01); *C07B 2200/13* (2013.01); *C07C 2601/16* (2017.05)

(58) Field of Classification Search
None
See application file for complete search history.

(56) References Cited

U.S. PATENT DOCUMENTS

| 6,818,798 B1 * | 11/2004 | Khachik | ................. C12P 23/00 435/67 |
| 2005/0153002 A1 * | 7/2005 | Socla Rosales | ....... A61K 36/28 435/67 |
| 2014/0303406 A1 * | 10/2014 | Lu | ......................... C07C 403/24 568/816 |

FOREIGN PATENT DOCUMENTS

CN    109053517 A    * 12/2018    ........... C07C 403/24

* cited by examiner

*Primary Examiner* — Nghi V Nguyen
(74) *Attorney, Agent, or Firm* — Ashok Tankha

(57) ABSTRACT

A method for extracting and isolating a lutein crystal from a vegetable oil resin containing a lutein diester, comprises: dissolving lipase into deionized water to form an enzyme solution; dissolving a lutein extract into an alcohol solvent containing the deionized water to form a uniform alcohol solution; adding the enzyme solution to the alcohol solution for performing hydrolysis, and stirring same to obtain a lutein solution; filtering and performing filtration isolation on the lutein solution to obtain a crystalline; re-dissolving the crystalline into a non-polar organic solvent, and using deionized water for washing a water-soluble impurity; recycling and cooling the organic solvent to obtain a recrystallization; and isolating and drying the recrystallization to obtain the lutein crystal. In this method, selectivity is strong, reaction time is short, no waste water is produced, process is environment-friendly and suitable for industrial production, and obtained lutein crystal is high in purity and yield.

12 Claims, No Drawings

METHOD FOR EXTRACTING AND ISOLATING LUTEIN CRYSTAL FROM VEGETABLE OIL RESIN CONTAINING LUTEIN DIESTER

CROSS-REFERENCE TO RELATED APPLICATIONS

This is a national phase application of PCT application number PCT/CN2019/095327, filed in the State Intellectual Property Office of China on Jul. 9, 2019, titled "Method For Extracting And Isolating Lutein Crystal From Vegetable Oil Resin Containing Lutein Diester", which claims priority to and benefit of Chinese patent application No. 201810753839.0 filed on Jul. 10, 2018 and Chinese patent application No. 201810992984.4 filed on Aug. 29, 2018. The specifications of the above referenced patent applications are incorporated herein by reference in their entirety.

FIELD OF THE INVENTION

The present invention relates to a method for catalyzing, isolating and purifying lutein and zeaxanthin with higher yield from vegetable oil resin especially marigold oil resin by using metagenomic library esterase (lipase).

BACKGROUND OF THE INVENTION

Carotenoids are yellow and red substances widely present in nature. There are different kinds of carotenoids such as β-carotene in carrots, lutein in marigold flowers, zeaxanthin in strawberries, lycopene in tomatoes, higher content capsicum red pigment and chili pigment in peppers in different fruits and vegetables. There are more carotenoids in some dark fruits and vegetables, egg yolks, fish, crustaceans, birds, seaweeds and bacteria, wherein the content of lutein is also higher.

In recent years, some animal and human experiments have shown the beneficial effects of carotenoids. In general, carotenoids may be divided into two sub-categories, that is, lutein with relatively strong polarity or oxygen-containing carotenoids such as lutein, zeaxanthin, astaxanthin etc., and nonpolar hydrocarbon carotenoids such as β-carotene, lycopene, etc. The carotenoids of these two subclasses contain at least nine conjugated double bonds. These conjugated double bonds not only give the carotenoids their color characteristics, but also make it have a strong antioxidant function in disease prevention and treatment. They can restrain or prevent diseases such as cancer, arteriosclerosis, cataract, splash degradation and other diseases. Moreover, carotenoids can limit the oxidative damage of free radicals, due to the ability of carotenoids having eliminating highly active oxygen free radicals and preventing free radical generation.

Among all carotenoids, lutein and zeaxanthin are attracting more and more attention from scientists and the public, because of its potential to prevent age-related macular degeneration (ARMD). Lutein and zeaxanthin is the only exists in the human retina spot area of carotenoids, and this area is closely related to people's visual acuity (Bone et al. Invest. Ophthamal. Vis. Sci. 34: 2033-2040, 1993). Often eat rich in lutein and corn yellow fruits and vegetables can reduce the risk of senile plaques degeneration diseases 43% (Seddon et al. J.Am.Med.Assoc.272:1413-1420, 1994). Moreover, now these compounds in preventing senile plaques degeneration disease metabolic pathway has been clear. The United State Food and Drug Administration also consider that lutein and zeaxanthin "generally recognized safe" (GARS). Therefore, these carotenoids can alone or together with other material used as nutritional supplements and food colorants, can also be applied to clinical prevention senile plaques degradation and cancer, etc.

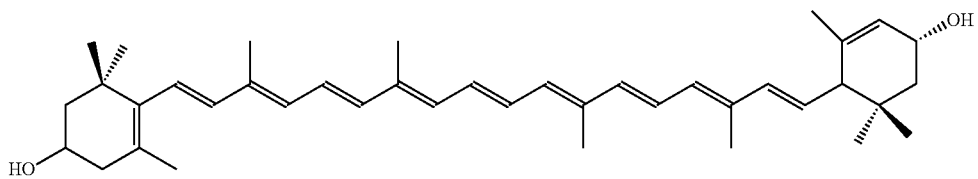

Lutein (molecular formula: $C_{40}H_{56}O_2$, molecular weight: 568.85)

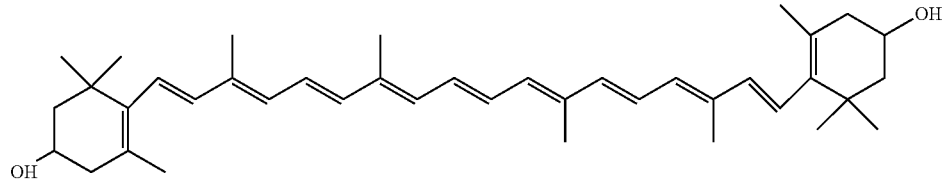 [SMILES: CC1=C(/C=C/C(C)=C/C=C/C(C)=C/C=C/C=C(C)/C=C/C=C(C)/C=C/C2=C(C)CC(O)CC2(C)C)C(C)(C)CC(O)C1]

Zeaxanthin (molecular formula: $C_{40}H_{56}O_2$, molecular weight: 568.85).

Since the chemical synthesis of lutein involves more steps, time consuming, high cost, it is economical and easy to mass production to obtain a large number of lutein crystals by extraction, separation and purification from natural resources.

Many vegetables and fruit, such as spinach, broccoli, cabbage and corn contain more lutein, but marigold flowers and calendula are the richest sources of lutein. Of course, there are other classes carotenoids in these plants. Lutein in plants are often esterified with some C12-C18 long-chain fatty acids such as myristic acid, oleic acid, linoleic acid and palmitic acid to exist in the form of monoester or diester.

The typical structural formula of lutein fatty acid diester is shown in the following formula.

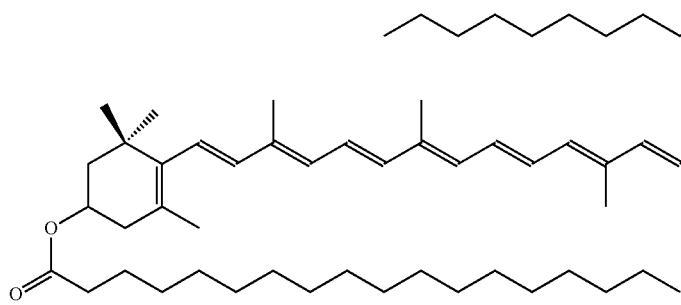

The structural formula of lutein dipalmitate ($C_{72}H_{116}O_4$, $M=1045.71$).

In order to obtain high-purity lutein crystals, the prior art generally uses organic solvents to extract lutein fatty acid esters from plants preferably marigold flowers, calendulas and other dark green vegetables. It would be easy to separate organic solvent itself. Marigold flower extract (marigold oil resin) is good sources of lutein esters, and the content of other carotenoids is relatively low. The mixture containing lutein fatty acid esters after recovery of organic solvent is in the form of a paste, generally called "marigold extract", or "marigold flower extract", or "lutein extract", or "lutein oil cream", or "lutein oil resin" (hereinafter collectively referred to as "lutein extract"), in which the content of lutein fatty acid esters is generally about 30%. In addition to lutein fatty acid esters, others also include vegetable waxes, fat-soluble compounds such as other fatty acids, and these have complex ingredients and an unpleasant smell.

Lutein fatty acid esters in the lutein extract are hydrolyzed under alkaline conditions, and the lutein crystals come off. After the fatty acid salt obtained by the saponification is washed away, the lutein crystals may be further purified, to finally obtain high quality lutein crystals.

At present, there are a large number of patents and documents related to methods for large-scale separation of lutein crystals from lutein extract by chemical method. The purpose of these documents is generally to obtain a pure lutein crystal form, and uses multiple separation steps.

U.S. Pat. No. 5,382,714 describes that the marigold oil resin after strong alkali saponification is washed with water at a relatively low temperature and crystallized in a mixed solvent at low temperature to separate and purify lutein. The purification process is not only time-consuming, but also the product obtained is not suitable for food and medicine because of using chlorine-containing organic solvents.

U.S. Pat. No. 5,648,564 describes a method for separating lutein crystals. Firstly, lutein diesters in a propylene glycol solution of marigold oil resin are saponified with a strong base, and then recrystallized. But the process also has several disadvantages: firstly, using a high concentration of strong base has a certain destructive effect on lutein with more unsaturated double bonds and reduces the yield of the final product; secondly, due to using propylene glycol having higher viscosity, the temperature in the process of saponification and subsequent treatment is required to be higher. The entire system should be kept at above 70° C. of temperature for about 10 hours. But it is obviously unfavorable to the stability of lutein. Cis-trans isomers of lutein will also change, and subsequent separation processes such as centrifugation or filtration are also more difficult; finally, the yield of lutein is lower, only about 59%, and the content of lutein in the product is not high.

U.S. Pat. No. 6,262,284 describes using tetrahydrofuran and simultaneously extracting carotenoids from dried marigold flowers and using strong alkali to saponify carotenoids. Using a large amount of organic solvents in this process is not good for stability of lutein and then lead to product degradation due to over-oxidation.

U.S. Pat. No. 6,380,442 reported a method for separating carotenoids from plants. The method is not very attractive in industrial production, because a large amount of water (at least 30 times the amount of raw materials) is used in the production process, and the operation is more difficult.

U.S. Pat. No. 6,743,953 uses several organic solvents to separate and purify lutein from marigold oil resin. A large amount of strong bases and various organic solvents such as isopropanol, ethyl acetate, n-hexane, acetone and methanol are used in this process. The operation is complicated, the organic solvent consumption is large, and the yield is low. Therefore, the method is not suitable for industrial production.

In summary, the methods described in the above patents have the following disadvantages: 1) a large amount of strong alkali is used in the process to saponify lutein fatty acid esters, and the presence of a large amount of strong alkali can easily to degrade lutein fatty acid ester and lutein with more unsaturated double bonds at higher reaction temperature, and consequently reduce the yield of the final product; 2) due to using the chemical alcoholysis process, a large amount of waste water is generated in the process to make environment not green and environmental protection; 3) it makes the product lutein crystals unsuitable for human consumption, because some toxic solvents used are difficult or impossible to completely be removed; and it is difficult to operate separation and purification because of using high viscosity of the organic solvents. It would need a multi-step crystallization process to obtain high content crystals, but it would not be suitable for industrial production; 4) the yield of lutein is low and then the product yield is low, only about 50%, due to the multiple steps involved in the process.

Therefore, it is necessary to find a method suitable for industrial scale production of high-purity lutein and zeaxanthin, in particular, no inorganic or organic alkali is used, but lutein fatty acid ester is hydrolyzed to free lutein under mild conditions by using biological enzyme preparation, and less toxic organic solvent is used in operation steps, but produces a higher yield of the product.

There have also been a small number of reports on uses of biological methods of extracting lutein crystals in the previous literature. Please refer to the following documents.

The Chinese Patent No. CN 101532045B describes an enzymatic method of extracting lutein, in particular, mixing marigold flower with an aqueous solution of angel yeast powder, successively adding ethanol and dry powder activated after fermentation, filtering and drying to obtain lutein crystals with the content of 50-60%, and the yield of 9.5-13%.

The Chinese Patent No. CN 101235409B discloses a method of preparing crystal lutein by enzymatic hydrolysis, in particular, lutein esterase is enzymatically hydrolyzed by using enzyme solution produced by mushroom fungus mycelium, and then crystallization, purification and drying to obtain lutein crystals. However, it needs keeping pH during the enzymatic hydrolysis process, and continuously adding 40% KOH or other strong alkali solution.

The Chinese Patent No. CN 107475343A provides a method of extracting lutein from marigold flowers, comprising fermentation, enzymolysis, supercritical extraction, vacuum freeze-drying and other steps. In particular, fermenting and converting lutein esters into free lutein by using yeast powder instead of the saponification reaction. But the reaction specificity is poor and the efficiency is poor. In order to improve the conversion efficiency, a certain amount of active short peptide must be added, and the reaction time is long, for more than 7 days, organic solvents and cellulase are added after the reaction, followed by supercritical $CO_2$ extraction, and vacuum freeze-drying. It may be seen from it that the operation steps are very complicated, and the final lutein content and yield are not high.

In the above method, lutein fatty acid ester is hydrolyzed into lutein by using primary fermentation enzyme liquid produced by yeast powder or mushroom fungus mycelium. But the fermentation time is very long, even more than 10 days, and a lot of impurities are produced, and complicated steps are required for purification operations, resulting in a low yield of the final product, because these primary fermentation enzyme liquids have low activity and poor specificity. In addition, in order to control the pH value of the reaction solution, a high concentration of alkali must be continuously added. This is also detrimental to the stability of lutein containing more unsaturated double bonds.

SUMMARY OF THE INVENTION

In order to overcome the shortcomings of producing lutein crystals by the chemical alcoholysis of the prior art and easily producing a large amount of waste water and low product yield caused by strong alkalinity as well as producing lutein crystals by biological enzymes of the prior art having low efficiency and poor specificity low yield, the present invention provides a suitable, easy-to-industrial production of efficiently producing lutein crystals by using a self-made esterase (lipase) derived from metagenomic library. The lipase has been published in CN102796715B.

The product obtained by the present invention can be used for human consumption. The content of lutein is more than 80%, wherein all-trans lutein accounts for at least 90%, the rest is zeaxanthin, a small amount of cis-lutein and other carotenoids.

The present invention provides a method for extracting and isolating lutein crystal from vegetable oil resin containing lutein diester, comprising the following steps: a) dissolving lipase into deionized water to form an enzyme solution; b) dissolving a lutein extract into an alcohol solvent containing a small amount of a deionized water at a temperature of 30~65° C. to form a uniform alcohol solution; c) adding the enzyme solution to the alcohol solution for performing a hydrolysis reaction at a temperature of 30~65° C. under stirring, until the lutein fatty acid ester completely hydrolyzed to lutein, to obtain a lutein solution; d) immediately filtering the lutein solution at a temperature of 30~65° C., and separating by pressure filtration to obtain a lutein crystal filter cake; e) re-dissolving the lutein crystal filter cake into a non-polar organic solvent at a temperature of 20-110° C., and washing by using a deionized water to remove a water-soluble impurity; f) recycling the non-polar organic solvent and cooling same to obtain a recrystallization; and g) isolating the recrystallization and then vacuum dried or freeze dried, to obtain lutein crystals, a final drying weight loss of the lutein crystals is less than 5%. In this process, the carotenoid ester in the lutein extract and the alcohol solvent containing a small amount of water are combined into a homogeneous solution, and then add a lipase aqueous solution to the homogeneous solution at a temperature of 30~65° C. After the reaction is completed, filter to obtain a solid filter cake. The solid filter cake is dissolved in a insoluble organic solvent, washed with water to remove residual lipase and a small amount of water-soluble impurities, and then recover part of the solvent, and cool temperature to crystallize, and then to produce crystals by centrifugation or filtration. The crystals obtained are recrystallized by using anhydrous ethanol and then dried to obtain a yellow to red fine powder crystal product.

The present invention uses extracts separated and purified by natural resources such as marigold, calendula, spinach, strawberry, broccoli, cabbage and corn, which contains large amounts of lutein esters, to obtain lutein and zeaxanthin. Among these raw materials, the lutein content in marigold extract is relatively higher. And consequently marigold is a priority raw material.

In the present invention, edible marigold oil resin extracted by n-hexane is used as the starting material for separating products with higher all-trans lutein content. Depending on variety, planting conditions, harvest time and extraction method, the oil resin contains 5-30% lutein lipids and a small amount of other carotenoids such as all-trans zeaxanthin, α-cryptoxanthin and β-cryptoxanthin and β-carotene and so on.

In the present invention, preferably, the lipase is dissolved in deionized water to obtain a lipase solution, and a volume of the deionized water is 5-250 times a weight of the lipase. The lipase is a homemade esterase (lipase) Est076 (C23) developed by professor Xie Tian of Hangzhou Normal University and has been disclosed in the Chinese Patent No.CN102796715B.

Preferably, the lutein extract is dissolved in an alcohol solvent containing a small amount of water to form a uniform solution within a temperature range of 30~65° C., and a content of the deionized water in the alcohol solvent is 5-15% (w/w). In general, one weight of lutein extract is dissolved in 0.5-8.0 times a volume of the alcohol solvent. Lutein esters and other impurities such as wax, resin, other carotenoids and pigments are dissolved or dispersed under stirring in the alcohol solvent to form a uniform solution.

Preferably, the alcohol solvent is selected from one of ethanol, n-propanol, isopropanol, and propylene glycol. Preferably, the enzyme solution is added to an uniformly dispersed lutein extract solution, and an amount of the lipase is 0.1-3.0% of a weight of the lutein extract. Stirring uniformly at 30-65° C. for 6-18 hours until the reaction is completed. The thin-layer chromatography will monitor whether the hydrolysis reaction is completed. After the hydrolysis reaction is completed, lutein, zeaxanthin and other carotenoids are separated and precipitated. At the same time, the fatty acids such as myristic acid, palmitic acid, and stearic acid in the lutein extract are also released and dissolved in reaction solvent. The reaction liquid is filtered to obtain a solid lutein crystal filter cake generated by the reaction.

Preferably, the lutein crystal filter cake is re-dissolved in a non-polar organic solvent to form a lutein solution, and wherein an amount of the organic solvent is 3-10 times (v/w) a weight of the lutein crystal filter cake. The temperature of the lutein crystal filter cake dissolved in the non-polar organic solvent is 30-80° C. The non-polar organic solvent is selected from one or two of ethyl acetate, isobutyl acetate, n-hexane, n-heptane, and dichloromethane.

Preferably, the deionized water is added to the lutein solution for washing to remove residual lipase and water-soluble impurities.

Preferably, the organic solvent is partly recovered to make the lutein content in the lutein solution after recovering of the organic solvent is 10-80 wt. %, and the temperature is lowered for crystallization, and the crystallization temperature is between −20° C. and 35° C. Lutein crystals are separated to obtain lutein crystals through traditional separation processes such as centrifugation, filtration, and pressure filtration. Lutein crystal powder is dried by conventional vacuum drying method.

It is known from the ultraviolet-visible light spectrophotometric analysis and HPLC analysis that a final product contains 80-95% carotenoids including 90-95% all-trans lutein, 0.1-1.0% of its geometric isomers, and 2.0-7.0% all-trans zeaxanthin and less than 1.0% other carotenoids. These tiny amounts of other carotenoids don't have to be harmful at all, because they are also dietary sources themselves, and they are found that their concentration in human serum is much higher than that of lutein.

Since strong alkali and high temperature are not used in the production process, only the specific new lipase is used to hydrolyze the ester bond of the lutein fatty acid ester. The reaction condition of the present invention is mild. Lutein fatty acid ester as a reaction substrate and Lutein crystals as the reaction product are less damaged. In addition, selecting the alcohol solvent containing specific water content as the reaction solvent during the reaction is very critical to a smooth progress of the reaction. The reason why we choose the alcohol solvent is that it has been found that the alcohol solvent has better solubility to lutein extract in experiment. The free fatty acids can also be completely dissolved in the plant waxes at relatively high temperatures, and the solubility of free lutein crystals in it after alcoholysis is relatively small. The solubility characteristics of the alcohol solvent are very beneficial to a smooth progress of the reaction and the precipitation of lutein crystals produced by the reaction, so that the subsequent purification steps are much simpler after the reaction is completed, that is, it only needs to re-dissolve precipitated lutein crude in a non-polar organic solvent, and then wash off residual lipase and water-soluble impurities with water to make the lutein content of the final product reach more than 80%. It was found through experiments that the water content in the alcohol solvent should be controlled within a range of 5-15% during the reaction. This is mainly because a certain amount of water molecules are needed to hydrolyze the ester bonds in the lutein fatty acid by using biological lipase. And the lipase should also be dissolved in a certain amount of water, but the water content in the reaction system should not be too high, because the water content is higher, it will affect the solubility of lutein fatty acid ester in it, thereby affecting reaction thoroughly. Moreover, if the water content is too high, it will result in easily precipitating impurities and reduce the purity of final product. Considering that the lipase must be dissolved in a certain amount of deionized water and then add the enzyme solution to the reaction solution, it needs to make appropriate adjustment the water content in the alcohol solvent based on the concentration of the enzyme solution.

It is based on new lipases derived from the above specific metagenomic origin and selection of specific alcohol solvent containing a certain amount of water that the lutein fatty acid ester in marigold oil resin has a strong specificity reaction under mild conditions. The reaction is completed in a relatively short time, no waste water is produced in the process, the process is green and environmentally friendly, and the lutein crystals obtained have high purity and high yield, and are suitable for industrial production.

The present invention provides a convenient and easy-to-industrial production method for efficiently extracting lutein crystals from vegetable oil resin containing lutein diester by using lipase. In this process, a homemade esterase (lipase) derived from a metagenomic library is used to hydrolyze lutein fatty acids into lutein crystals. The reaction conditions are mild, the reaction efficiency is high, and the minimum organic solvents are used, the purification steps are simple, and the product of the yield is high. The advantages of the present invention are embodied in the following aspects: firstly, the lutein fatty acid ester in the lutein extract is hydrolyzed by the homemade esterase (lipase) derived from the metagenomic library. The reaction conditions are mild to overcome the damage of lutein by adding high-alkaline in saponification of the chemical method, it is beneficial to improve product yields; secondly, the applied new recombinant lipase has high activity, strong specificity and high reaction efficiency; thirdly, selecting a specific concentration of alcohol solvent is not only beneficial to dissolve both biological lipase and lutein extract as reaction substrate and impurity plant waxes and free fatty acids released by the reaction, but also beneficial to precipitate lutein crystals as reaction product and the purification of the product; fourthly, subsequent purification steps are also very simple and easy for industrial production. The content and yield of the final product in the present process can respectively reach 80% and 85%, which are higher than that of the prior art. Therefore, the process of the present invention is very economical and suitable for large-scale commercial production. These and other advantages will be well reflected in the subsequent description of the present invention.

DESCRIPTION OF EMBODIMENTS OF THE INVENTION

To further illustrate the present invention, a series of embodiments are given below. These embodiments are purely illustrative and are used only as a specific description of the present invention and should not be construed as a limitation of the present invention.

Example 1

To dissolve 1 g of recombinant new esterase (lipase) Est076 (C23) constructed by Professor Xie Tian of Hangzhou Normal University to 95 ml of water to form an enzyme solution. 1000 g marigold oil resin (15.8% of total lutein content, purchased from Qingdao Saite Perfume Co., Ltd.) is mixed with 2250 mL of absolute ethanol. At the beginning of the reaction, the water content of the alcohol solvent is 5.1%, and then raise a temperature to 65° C. under stirring until form a uniformly flowing solution, and afterwards add the enzyme solution to the uniformly flowing solution, at the same time monitor the extent of the reaction by the thin-layer chromatography. After 18 hours, the lutein fatty acid ester is completely hydrolyzed, and then stop stirring and let stand for 0.5 hr.

The reaction solution is cooled to 65° C. and immediately filtered at 65° C. to obtain 305.6 g of a yellow filter cake. The filter cake is added to 1000 ml ethyl acetate, heated to 70° C. to dissolve, and then wash three times with 500 ml deionized water and separate water layers. And then recover 900 ml of ethyl acetate, and afterwards cool to a temperature of −20° C. for freezing and crystallization. After the crystallization is completed, centrifugal separation, vacuum drying, until the dry weight loss is less than 5%.

Finally, to obtain 150.7 g of finished product wherein containing 85.2% total carotenoids (analyzed by UV-visible spectrophotometer), these carotenoids comprise 91.8% all-trans lutein and 4.5% all-trans zeaxanthin (analyzed by HPLC), and the rest are trace amounts of other carotenoids. The total yield of lutein is 85%.

The finished product does not contain toxic organic solvents and is suitable for use in the form of nutritional supplements and food additives. The application form of the crystal may be oil suspension (mixed and emulsified with vegetable oil), beads (microcapsules obtained by spray condensation), dry powder (microcapsules obtained by spray drying), etc.

Example 2

To dissolve 15 g of recombinant new esterase (lipase) Est076 (C23) constructed by Professor Xie Tian of Hangzhou Normal University to 988 ml of water to form an enzyme solution. 1000 g marigold oil resin (15.8% of total lutein content, purchased from Qingdao Saite Perfume Co., Ltd.) is mixed with 8000 mL of 98.5% n-propanol, and then raise a temperature to 65° C. under stirring until form a uniformly flowing solution, and afterwards add the enzyme solution to the uniformly flowing solution, at the same time monitor the extent of the reaction by the thin-layer chromatography. After 6 hours, the lutein fatty acid ester is completely hydrolyzed, and then stop stirring and let stand for 0.5 hr. At the beginning of the reaction, the water content of the alcohol solvent is 15.0%.

The reaction solution is cooled to 30° C. and immediately filtered at 30° C. to obtain 321.4 g of a yellow filter cake. The filter cake is added to 3200 ml isobutyl acetate, heated to 110° C. to dissolve, and then wash three times with 800 ml deionized water and separate water layers. And then recover 2400 ml of isobutyl acetate, and afterwards cool to a temperature of −18° C. for freezing and crystallization. After the crystallization is completed, centrifugal separation, vacuum drying, until the dry weight loss is less than 5%.

Finally, to obtain 162.1 g of finished product wherein containing 81.6% total carotenoids (analyzed by UV-visible spectrophotometer), these carotenoids comprise 90.9% all-trans lutein and 5.4% all-trans zeaxanthin (analyzed by HPLC), and the rest are trace amounts of other carotenoids.

The finished product does not contain toxic organic solvents and is suitable for use in the form of nutritional supplements and food additives. The application form of the crystal may be oil suspension (mixed and emulsified with vegetable oil), beads (microcapsules obtained by spray condensation), dry powder (microcapsules obtained by spray drying), etc.

Example 3

To dissolve 30 g of recombinant new esterase (lipase) Est076 (C23) constructed by Professor Xie Tian of Hangzhou Normal University to 120 ml of water to form an enzyme solution. 1000 g marigold oil resin (15.8% of total lutein content, purchased from Qingdao Saite Perfume Co., Ltd.) is mixed with 3000 mL of propylene glycol containing 10.0% deionized water, and then raise a temperature to 30° C. under stirring until form a uniformly flowing solution, and afterwards add the enzyme solution to the uniformly flowing solution, at the same time monitor the extent of the reaction by the thin-layer chromatography. After 15 hours, the lutein fatty acid ester is completely hydrolyzed, and then stop stirring and let stand for 0.5 hr.

The reaction solution is cooled to 60° C. and immediately filtered at 60° C. to obtain 297.6 g of a yellow filter cake. The filter cake is added to 1000 ml dichloromethane, to dissolve at 20° C., and then wash three times with 900 ml deionized water and separate water layers. And then recover 750 ml of dichloromethane, and afterwards cool to a temperature of −4° C. for freezing and crystallization. After the crystallization is completed, centrifugal separation, vacuum drying, until the dry weight loss is less than 5%.

Finally, to obtain 142.6 g of finished product wherein containing 80.9% total carotenoids (analyzed by UV-visible spectrophotometer), these carotenoids comprise 92.1% all-trans lutein and 4.3% all-trans zeaxanthin (analyzed by HPLC), and the rest are trace amounts of other carotenoids.

Example 4

To dissolve 15 g of recombinant new esterase (lipase) Est076 (C23) constructed by Professor Xie Tian of Hangzhou Normal University to 250 ml of water to form an enzyme solution. 1000 g marigold oil resin (15.8% of total lutein content, purchased from Qingdao Saite Perfume Co., Ltd.) is mixed with 3000 mL of isopropanol containing 10.0% deionized water, and then raise a temperature to 45° C. under stirring until form a uniformly flowing solution, and afterwards add the enzyme solution to the uniformly flowing solution, at the same time monitor the extent of the reaction by the thin-layer chromatography. After 10 hours, the lutein fatty acid ester is completely hydrolyzed, and then stop stirring and let stand for 0.5 hr.

The reaction solution is cooled to 45° C. and immediately filtered at 45° C. to obtain 303.5 g of a yellow filter cake. The filter cake is added to 3000 ml of mixture of n-hexane and n-heptane (7:3), to dissolve at 45° C., and then wash three times with 900 ml deionized water and separate water layers. And then recover 1600 ml of organic solvent, and afterwards cool to a temperature of 35° C. for freezing and crystallization. After the crystallization is completed, centrifugal separation, vacuum drying, until the dry weight loss is less than 5%.

Finally, to obtain 156.1 g of finished product wherein containing 87.2% total carotenoids (analyzed by UV-visible spectrophotometer), these carotenoids comprise 91.2% all-trans lutein and 5.6% all-trans zeaxanthin (analyzed by HPLC), and the rest are trace amounts of other carotenoids.

Example 5

To dissolve 12 g of recombinant new esterase (lipase) Est076 (C23) constructed by Professor Xie Tian of Hangzhou Normal University to 140 ml of water to form an enzyme solution. 1000 g marigold oil resin (15.8% of total lutein content, purchased from Qingdao Saite Perfume Co., Ltd.) is mixed with 4800 mL propylene glycol containing 15.0% deionized water, and then raise a temperature to 45° C. under stirring until form a uniformly flowing solution, and afterwards add the enzyme solution to the uniformly flowing solution. At the beginning of the reaction, the water content of the alcohol solvent is 18%, at the same time monitor the extent of the reaction by the thin-layer chromatography. After 16 hours, there is still a small amount of lutein fatty acid ester not hydrolyzed completely, and then stop stirring and let stand for 0.5 hr.

The reaction solution is heated to 60° C. and immediately filtered at 60° C. to obtain 380.0 g of a yellow filter cake. The filter cake is added to 3600 ml of mixture of n-hexane and n-heptane (7:3), to dissolve at 45° C., and then wash three times with 900 ml deionized water and separate water layers. And then recover 1600 ml of organic solvent, and afterwards cool to a temperature of 35° C. for freezing and crystallization. After the crystallization is completed, centrifugal separation, vacuum drying, until the dry weight loss is less than 5%.

Finally, to obtain 132.5 g of finished product wherein containing 68.4% total carotenoids (analyzed by UV-visible spectrophotometer).

Example 6

To dissolve 30 g of recombinant new esterase (lipase) Est076 (C23) constructed by Professor Xie Tian of Hangzhou Normal University to 120 ml of water to form an enzyme solution. 1000 g marigold oil resin (15.8% of total lutein content, purchased from Qingdao Saite Perfume Co., Ltd.) is mixed with 3000 mL absolute ethanol, and then raise a temperature to 30° C. under stirring until form a uniformly flowing solution, and afterwards add the enzyme solution to the uniformly flowing solution. At the beginning of the reaction, the water content of the alcohol solvent is 4.88%, at the same time monitor the extent of the reaction by the thin-layer chromatography. The enzyme is found to have failed to dissolve completely, and a small amount of particles are suspended in it. After 18 hours, there is still a small amount of lutein fatty acid ester not hydrolyzed completely, and then stop stirring.

It is required to be declared that the invention contents and specific examples are intended to prove the practical application of the technical solution provided by the present invention, and shall not be interpreted as a limitation of the protection scope of the present invention. It is easy for any persons skilled in the art to carry out further improvement and perfection not from the spirit and scope of the invention, so the present invention is just limited by the content and scope of claims of the present invention, its intention to cover all included all alternative solutions and equivalent solutions within the spirit and scope of the present invention limited by the appendix claims.

We claim:

1. A method for extracting and isolating lutein crystal from vegetable oil resin containing lutein diester, comprising the following steps:
    a) dissolving a lipase Est076 (C23) into deionized water to form an enzyme solution;
    b) dissolving a lutein extract into an alcohol solvent containing deionized water at a temperature of 30-65° C. to form a uniform alcohol solution, wherein the alcohol solvent is ethanol, isopropanol, n-propanol, or propylene glycol, and wherein the deionized water in the alcohol solvent is 5-15% (w/w);
    c) adding the enzyme solution to the alcohol solution for performing a hydrolysis reaction at a temperature of 30-65° C. under stirring, until the lutein fatty acid ester is completely hydrolyzed to lutein, to obtain a lutein solution;
    d) immediately filtering the lutein solution at a temperature of 30-65° C., and separating by pressure filtration to obtain a lutein crystal filter cake;
    e) re-dissolving the lutein crystal filter cake into a non-polar organic solvent at a temperature of 20-110° C., and washing using deionized water to remove a water-soluble impurity;
    f) partly recycling the non-polar organic solvent and cooling same to obtain a recrystallized crystals; and
    g) isolating the recrystallized crystals and then vacuum drying or freeze drying, to obtain lutein crystals, wherein a final dry weight loss of the lutein crystals is less than 5%.

2. The method of claim 1, wherein in step a), the lutein extract is an extract of marigold, calendula, spinach, strawberry, broccoli, cabbage, corn, containing a large amount of lutein esters.

3. The method of claim 1, wherein in step a), a volume of the deionized water is 5-250 times a weight of the lipase.

4. The method of claim 1, wherein in step b), an amount of the alcohol solvent containing the deionized water is 0.5-8.0 times (v/w) a weight of the lutein extract.

5. The method of claim 1, wherein in step c), an amount of the lipase is 0.1-3.0% of a weight of the lutein extract.

6. The method of claim 1, wherein in step c), a reaction time of the hydrolysis reaction is 6-18 hours.

7. The method of claim 1, wherein in step e), an amount of the non-polar organic solvent is 3-10 times (v/w) a weight of the lutein crystal filter cake.

8. The method of claim 1, wherein in step e), the temperature of the lutein crystal filter cake dissolved in the non-polar organic solvent is 30-80° C.

9. The method of claim 1, wherein in step e), the non-polar organic solvent is selected from one or two of ethyl acetate, isobutyl acetate, n-hexane, n-heptane, and dichloromethane.

10. The method of claim 1, wherein in step f), the lutein content in the lutein solution is 10-80 wt % after recovering the non-polar organic solvent.

11. The method of claim 1, wherein in step f), the crystallization temperature is in a range of −20° C. to +35° C.

12. The method of claim 1, wherein the lutein crystals are suitable for use in nutritional supplements and food additives in the form of oil suspension, beads, or dry powder.

* * * * *